United States Patent
Matsunaga et al.

(10) Patent No.: US 8,833,130 B2
(45) Date of Patent: Sep. 16, 2014

(54) TISSUE FASTNER PRODUCTION METHOD AND TISSUE FASTENER

(75) Inventors: Rei Matsunaga, Tokyo (JP); Masatoshi Sato, Yokohama (JP); Kunihide Kaji, Tokyo (JP); Shinji Takahashi, Tokyo (JP)

(73) Assignee: Olympus Medical Systems Corp., Tokyo (JP)

(*) Notice: Subject to any disclaimer, the term of this patent is extended or adjusted under 35 U.S.C. 154(b) by 0 days.

(21) Appl. No.: 13/357,954

(22) Filed: Jan. 25, 2012

(65) Prior Publication Data

US 2012/0215236 A1 Aug. 23, 2012

Related U.S. Application Data

(63) Continuation of application No. PCT/JP2011/064245, filed on Jun. 22, 2011.

(60) Provisional application No. 61/357,154, filed on Jun. 22, 2010.

(51) Int. Cl.
| | |
|---|---|
| *B21D 11/14* | (2006.01) |
| *B21F 3/04* | (2006.01) |
| *B21F 35/00* | (2006.01) |
| *B21F 45/00* | (2006.01) |
| *A61B 17/064* | (2006.01) |
| *A61B 17/11* | (2006.01) |
| *A61B 17/00* | (2006.01) |

(52) U.S. Cl.
CPC ..... *A61B 17/0644* (2013.01); *A61B 2017/0649* (2013.01); *A61B 17/1114* (2013.01); *B21F 35/00* (2013.01); *A61B 2017/00526* (2013.01); *A61B 2017/00867* (2013.01); *A61B 2017/00862* (2013.01); *B21F 45/008* (2013.01); *B21F 3/04* (2013.01); *A61B 2017/0645* (2013.01)
USPC ................... 72/371; 72/128; 72/135; 72/138; 140/71 C; 140/103

(58) Field of Classification Search
CPC ............... B21F 3/00; B21F 3/02; B21F 3/04; B21F 3/10; B21F 35/006; B21F 35/02

USPC .............. 72/128, 135, 137, 138, 371; 140/89, 140/71 C, 103, 124; 623/1.18, 1.19, 1.22; 600/140, 143; 606/139, 151
See application file for complete search history.

(56) References Cited

U.S. PATENT DOCUMENTS 3,987,386 A * 10/1976 Valliere ........................... 336/20
4,175,617 A * 11/1979 Hahn et al. ...................... 165/122
(Continued)

FOREIGN PATENT DOCUMENTS

| JP | 5-212065 | * | 8/1993 | ............... A61C 7/22 |
| JP | 5-212065 A | | 8/1993 | |

(Continued)

OTHER PUBLICATIONS

International Search Report PCT/JP2011/064245 dated Jul. 26, 2011together with English language translation.

(Continued)

*Primary Examiner* — Edward Tolan
(74) *Attorney, Agent, or Firm* — Scully, Scott, Murphy & Presser, PC

(57) ABSTRACT

A tissue fastener production method of clamping two living tissues together by bringing the two living tissues into close contact includes the following steps: fixing one end of a wire material made of a metal to a shaft body, and winding the wire material around an outer periphery of the shaft body while twisting the wire material round an axis of the wire material, thereby forming a coil on which a predetermined force is exerted in the winding direction; heat treating the wire material to impart superelasticity thereto; and deforming the wire material to which the superelasticity is imparted in a range in which the wire material is elastically deformable, and reversing the winding direction of the coil in a direction reverse to the winding direction of the coil wound in the step of forming the coil so as to obtain an initial tension corresponding to the predetermined force.

11 Claims, 11 Drawing Sheets

(56) References Cited

U.S. PATENT DOCUMENTS

| | | | | |
|---|---|---|---|---|
| 4,635,865 | A | * | 1/1987 | Arnold .................. 242/437.2 |
| 4,682,394 | A | * | 7/1987 | Wells et al. ............. 29/896.92 |
| 4,719,683 | A | * | 1/1988 | Ulbing .................. 29/896.9 |
| 6,375,628 | B1 | * | 4/2002 | Zadno-Azizi et al. ....... 600/585 |
| 6,458,092 | B1 | * | 10/2002 | Gambale et al. ............ 604/22 |
| 6,790,218 | B2 | * | 9/2004 | Jayaraman ................ 606/191 |
| 7,033,386 | B2 | * | 4/2006 | Richter et al. ............ 623/1.19 |
| 7,694,427 | B2 | * | 4/2010 | Long ..................... 33/520 |
| 8,162,958 | B2 | * | 4/2012 | Takahashi et al. ......... 606/139 |
| 2008/0015633 | A1 | * | 1/2008 | Abbott et al. ............ 606/207 |
| 2008/0097523 | A1 | * | 4/2008 | Bolduc et al. ............ 606/219 |
| 2010/0010514 | A1 | | 1/2010 | Ishioka et al. |

FOREIGN PATENT DOCUMENTS

| | | |
|---|---|---|
| JP | 2003-517869 A | 6/2003 |
| JP | 2004-508093 A | 3/2004 |
| JP | 2005-193044 A | 7/2005 |
| JP | 2009-66408 A | 4/2009 |
| JP | 2010-017542 A | 1/2010 |
| JP | 2010-501801 A | 1/2010 |
| WO | 02/17796 A1 | 3/2002 |
| WO | WO 02/19923 A1 | 3/2002 |

OTHER PUBLICATIONS

European Search Report dated Apr. 26, 2013 from corresponding European Patent Application No. 11 798 169.6.

* cited by examiner

TISSUE FASTNER PRODUCTION METHOD AND TISSUE FASTENER

This application is a continuation application based on a PCT patent Application No. PCT/JP2011/064245, filed Jun. 22, 2011, whose priority is claimed on U.S. Patent Provisional Application No. 61/357,154 filed on Jun. 22, 2010. The contents of both the PCT application and the US Patent Provisional Application are incorporated herein by reference.

BACKGROUND OF THE INVENTION

1. Field of the Invention

The present invention relates to a tissue fastener which clamps two living tissues together by bringing the two living tissues into close contact with each other and a production method thereof.

2. Description of Related Art

As a method of performing a treatment on an organ or the like of a human body, a laparoscopic surgery is known in which a treatment tool is percutaneously inserted. According to the laparoscopic surgery, an invasiveness of an operation is reduced compared to a case of making an incision in the abdomen, and fast recovery can be expected.

The treatment tool used in the laparoscopic surgery has a hard shaft inserted into the body percutaneously, and is generally provided with, for example, a forceps for performing a treatment on an organ or the like of the human body, at the distal end of the shaft.

For example, in Japanese Unexamined Patent Application, First Publication No. 2005-193044, an intraluminal anastomosis device used for the purpose of joining luminal tissues is disclosed. In the intraluminal anastomosis device, a gripping tool which is able to be freely opened and closed is mounted to the distal end of a shaft, and a clamp is inserted into the shaft. The clamp is produced by performing a heat treatment on a shape-memory alloy in a flat coil shape and is inserted into the shaft while being extended.

The clamp may be pushed out from the distal end of the shaft by an extrusion mechanism provided in the periphery of the intraluminal anastomosis device. For use of the clamp, the clamp is pushed out by the extrusion mechanism and is held in the body. The clamp is heated by the body heat and is restored to the coil shape so as to fasten the luminal tissues. Accordingly, the luminal tissues are joined to each other.

In addition, an example of supplying a clamp that clamps a living tissue into the body is disclosed in International Application No. 2002/019923. In International Application No. 2002/019923, a supply device which pushes the clamp out of a needle and supplies the clamp to the tissue is described, and it is described that a stopper that controls the depth by which the needle is inserted into the tissue and the amount of the clamp supplied into the tissue is provided.

When a treatment is performed using the supply device along with the clamp, by causing a mechanism accommodating the clamp and the needle to strike the tissue, the needle is advanced and the needle pierces and is inserted into the tissue. When the needle is inserted into the tissue, the position of the clamp is fixed by the stopper and the needle is pulled out from the tissue. Since the stopper is provided, the distal end part of the clamp remains inside the tissue due to the stopper. When the mechanism is excluded from the tissue, the remaining part of the clamp remains outside the tissue. In addition, when the clamp is restored to the coil shape, the tissue is clamped.

SUMMARY OF THE INVENTION

According to a first aspect of the present invention, a tissue fastener production method of clamping two living tissues together by bringing the two living tissues into close contact with each other, includes the following steps of: fixing one end of a wire material made of a metal to a shaft body, and winding the wire material around an outer periphery of the shaft body while twisting the wire material round an axis of the wire material, thereby forming a coil on which a predetermined force is exerted in an axial direction of the coil; after the step of forming the coil, heat treating the wire material to impart superelasticity thereto; and after the step of heat treating, deforming the wire material to which the superelasticity is imparted in a range in which the wire material is elastically deformable, and reversing the winding direction of the coil in a direction reverse to the winding direction of the coil wound in the step of forming the coil so as to obtain an initial tension corresponding to the predetermined force.

According to a second aspect of the present invention, a tissue fastener production method of clamping two living tissues together by bringing the two living tissues into close contact with each other, includes the following steps of: fixing one end of a wire material made of a metal to a shaft body, and winding the wire material around an outer periphery of the shaft body while opening a gap from the adjacent wire material, thereby forming a coil; after the step of forming the coil, heat treating the wire material to impart superelasticity thereto; and after the step of heat treating, deforming the wire material to which the superelasticity is imparted in a range in which the wire material is elastically deformable, and reversing the winding direction of the coil in a direction reverse to the winding direction of the coil wound in the step of forming the coil. In this aspect, after the step of reversing the winding direction of the coil, an initial tension is exerted on the coil in a compression direction of the coil.

According to a third aspect of the present invention, in the step of forming the coil in the first aspect of the present invention, the coil is formed with the following portions: a tissue fixing portion having a coil shape; a spring portion that is connected to the tissue fixing portion, is wound in the same direction as a winding direction of the tissue fixing portion, and is formed in a coil shape with a greater coil diameter than the coil diameter of the tissue fixing portion; and a tissue pressing portion that is connected to the spring portion, is wound in the same direction as the winding direction of the spring portion, and is formed in a coil shape with a greater coil diameter than the coil diameter of the spring portion.

According to a fourth aspect of the present invention, a tissue fastener having spring characteristics which clamps two living tissues together by bringing the two living tissues into close contact with each other, includes the following portions: a tissue fixing portion which has a first coil diameter and has a coil shape configured to bring the two living tissues into close contact with each other; a spring portion which is connected to the tissue fixing portion and has a second coil diameter greater than the first coil diameter of the tissue fixing portion; and a tissue pressing portion which is connected to the spring portion, has a third coil diameter greater than the second coil diameter of the spring portion, and is formed in a coil shape by the wire material.

In this aspect, in the tissue pressing portion, the wire material is wound along one or more circumferences in a helical shape with the third coil diameter, and in an unloaded state where an external force is not exerted on the tissue pressing portion, the adjacent wire materials have a gap in an axial direction of the coil.

DETAILED DESCRIPTION OF THE INVENTION

A tissue fastener 1 of a first embodiment of the present invention will be described.

Figure 1:
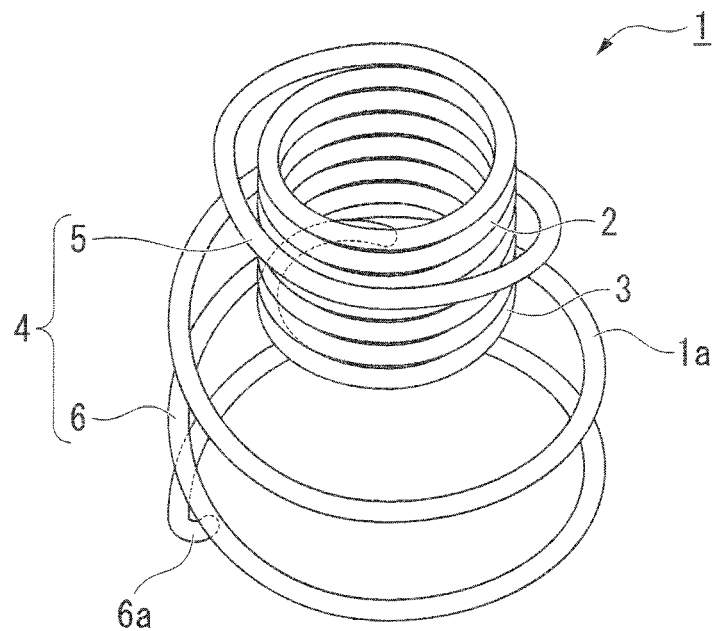
FIG. 1 is a perspective view illustrating a tissue fastener of an embodiment.
Figure 2:
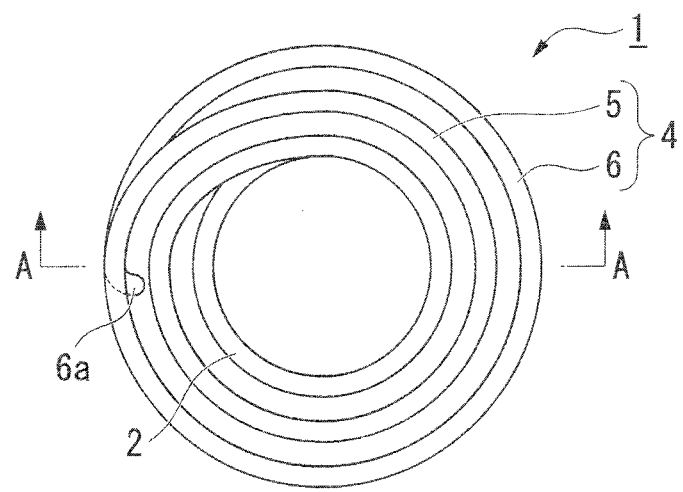
FIG. 2 is a plan view illustrating a shape of the tissue fastener viewed from a first tissue fixing portion side toward a second tissue fixing portion side.
Figure 3:
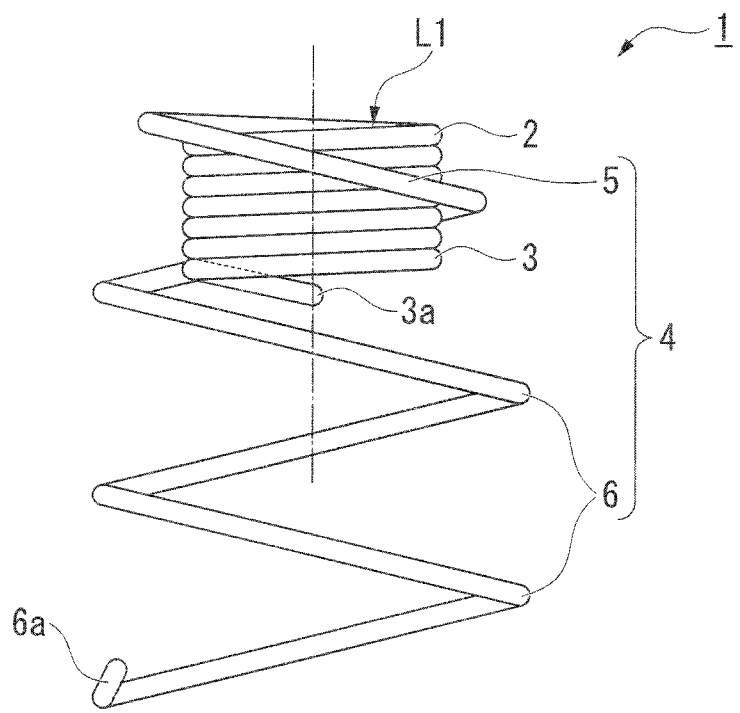
FIG. 3 is a side view illustrating the tissue fastener.
Figure 4A:
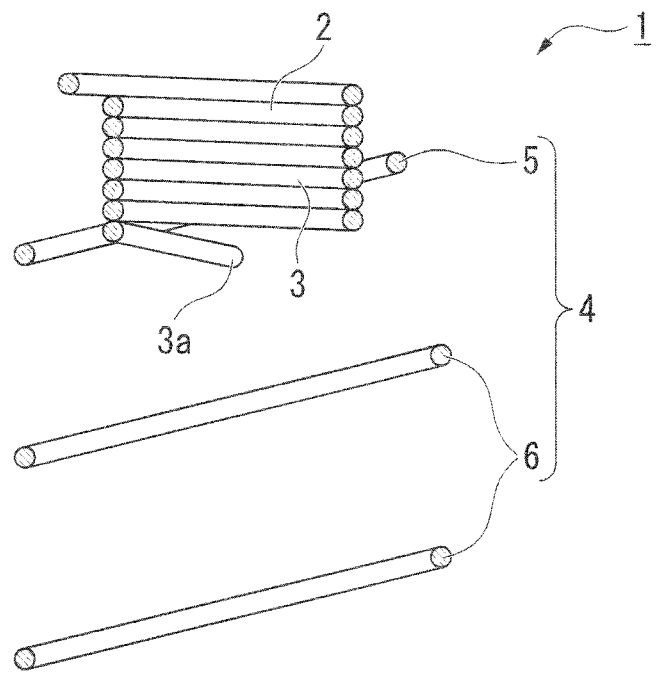
FIG. 4A is an explanatory view for explaining the operation of the tissue fastener of this embodiment and is a diagram illustrating the cross-section taken along the line A-A of FIG. 2.
Figure 4B:
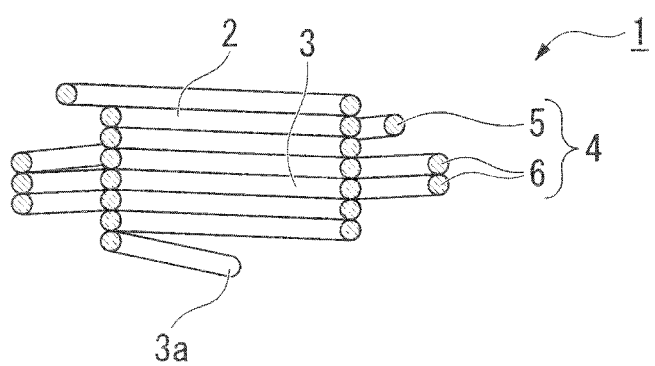
FIG. 4B is an explanatory view for explaining the operation of the tissue fastener of this embodiment and is a diagram illustrating the cross-section taken along the line A-A of FIG. 2.
Figure 5:
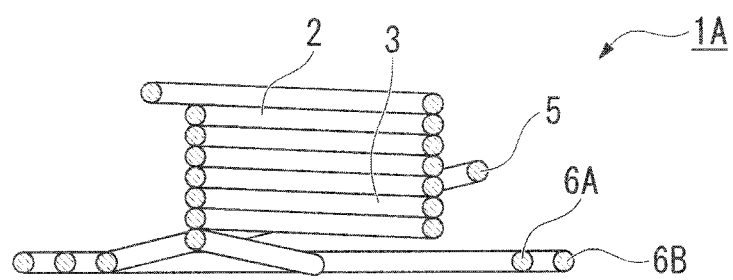
FIG. 5 is an explanatory view for explaining the operation of a tissue fastener according to related art.
Figure 6:
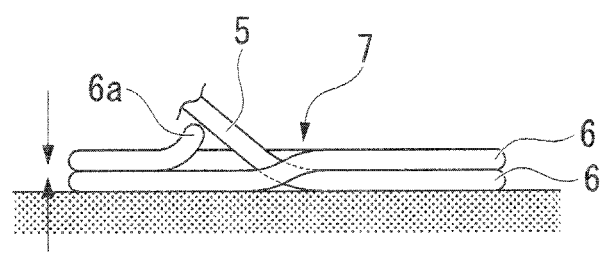
FIG. 6 is a side view illustrating the configuration of a part of the tissue fastener of this embodiment.
Figure 7A:
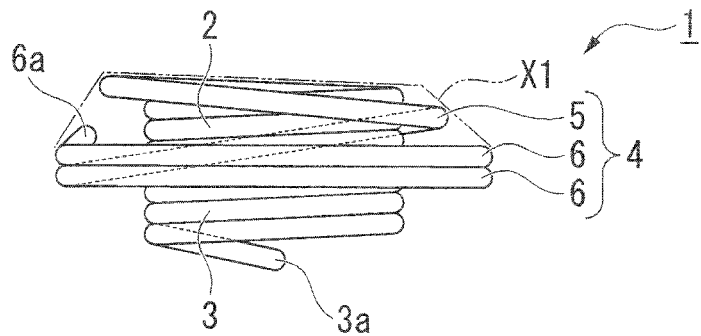
FIG. 7A is an explanatory view for explaining a form in use of the tissue fastener of this embodiment.
Figure 7B:
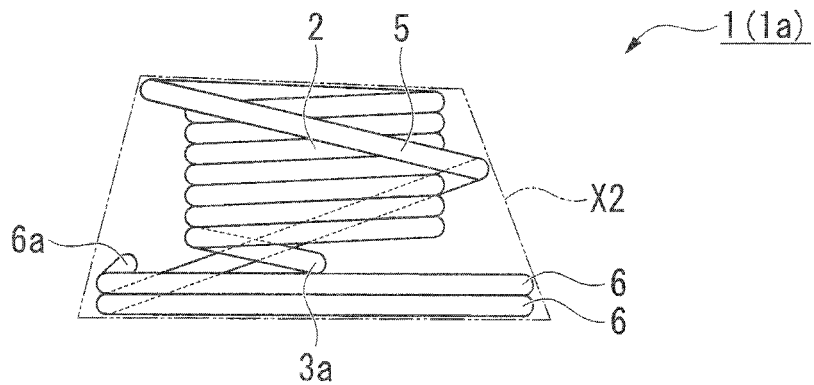
FIG. 7B is an explanatory view for explaining a form in use of the tissue fastener of this embodiment.
Figure 8:
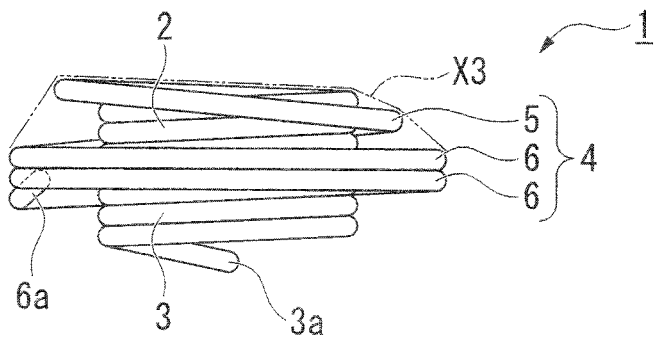
FIG. 8 is an explanatory view for explaining another form in use of the tissue fastener.

FIG. 1 is a perspective view illustrating the tissue fastener 1 of this embodiment. FIG. 2 is a plan view illustrating the shape of the tissue fastener 1 viewed from a first tissue fixing portion 2 side toward a second tissue fixing portion 3 side. FIG. 3 is a side view illustrating the tissue fastener 1. FIGS. 4A and 4B are explanatory views for explaining the operation of the tissue fastener 1 of this embodiment and are diagrams illustrating the cross-section taken along the line A-A of FIG. 2. FIG. 5 is an explanatory view for explaining the operation of a tissue fastener according to related art. FIG. 6 is a side view illustrating the configuration of a part of the tissue fastener 1 of this embodiment. FIGS. 7A and 7B are explanatory views for explaining a form in use of the tissue fastener 1 of this embodiment. FIG. 8 is an explanatory view for explaining another form in use of the tissue fastener 1.

The tissue fastener 1 of this embodiment is for fixing a first living tissue and a second living tissue in one body and providing a fistula for a part to which both the tissues are fixed. Here, the first and second living tissues are not limited to indication of different tissues. For example, an area of an organ may be referred to as a first living tissue, and another area of the same organ may be a second living tissue. In addition, a case where these two areas are fixed by causing each of the living tissues to be caught on the tissue fastener 1 of this embodiment is included in a procedure in this embodiment.

In this embodiment, a procedure of fixing a common bile duct as the second living tissue to a duodenum as the first living tissue and of providing a fistula for connecting both the organs is exemplified so as to describe the tissue fastener 1 of this embodiment.

First, the configuration of the tissue fastener 1 of this embodiment will be described.

As illustrated in FIG. 1, the tissue fastener 1 is formed of a single metal wire material 1a wound in a coil shape. The tissue fastener 1 includes the first tissue fixing portion 2 on which the duodenum is caught, the second tissue fixing portion 3 on which the common bile duct adjacent to the duodenum is caught, and an outer circumference spring portion 4 connected to the first tissue fixing portion 2. As the material of the metal wire material 1a of the tissue fastener 1, a superelastic alloy having superelasticity may be employed.

As illustrated in FIGS. 1 to 3, the first tissue fixing portion 2 and the second tissue fixing portion 3 are formed in a cylindrical coil shape of which the center axis line is positioned on the coaxial line thereof. In addition, the coil diameters of the first tissue fixing portion 2 and the second tissue fixing portion 3 are the same. In this embodiment, in the first tissue fixing portion 2 and the second tissue fixing portion 3, the winding direction of the metal wire material 1a is dextral.

Here, dextrality is a method of winding, to the upper right from the lower left, the metal wire material 1a viewed on the near side when the axial direction of the coil is the vertical direction. That is, it can be said that dextrality is a right hand winding direction and is a winding direction of a right screw. Otherwise, it can be said that the metal wire material 1a proceeds clockwise as it goes in the axial direction of the coil.

For example, as the metal wire material 1a is viewed in the axial direction of the coil, the proximal end of the metal wire material 1a is disposed on the near side and the distal end of the metal wire material 1a is wound dextrally inward from the near side, thereby forming a dextral coil.

In the tissue fastener 1, an initial tension is exerted on the first tissue fixing portion 2 and the second tissue fixing portion 3. The force of the initial tension in the first tissue fixing portion 2 and the second tissue fixing portion 3 is set to a force to the degree that the bloodstream in the living tissues can be impeded when the two living tissues are interposed between the first tissue fixing portion 2 and the second tissue fixing portion 3 and the two living tissues can be adhered to each other. The force of the initial tension of the first tissue fixing portion 2 and the second tissue fixing portion 3 is adjusted depending on the shape or kind of the living tissues which are objects to be interposed therebetween.

The outer circumference spring portion 4 includes a spring portion 5 extending from the end portion of the first tissue fixing portion 2, and a tissue pressing portion 6 extending from the end portion of the spring portion 5. In this embodiment, in the outer circumference spring portion 4, the winding direction of the metal wire material 1a is sinistral. The coil diameter of the outer circumference spring portion 4 is greater than those of the first tissue fixing portion 2 and the second tissue fixing portion 3.

Here, sinistrality is a method of winding, to the upper left from the lower right, the metal wire material 1a viewed on the near side when the axial direction of the coil is the vertical direction. That is, it can be said that sinistrality is a winding direction reverse to the right hand and a winding direction reverse to the right screw. Otherwise, it can also be said that sinistrality is a method of winding the metal wire material 1a to proceed counterclockwise as it goes in the axial direction of the coil.

For example, as the metal wire material 1a is viewed in the axial direction of the coil, the proximal end of the metal wire material 1a is disposed on the near side and the distal end of the metal wire material 1a is wound sinistrally inward from the near side.

The spring portion 5 is greater than the first tissue fixing portion 2 and the second tissue fixing portion 3 in coil diameter and extends from the end portion of the first tissue fixing portion 2 toward the second tissue fixing portion 3. Furthermore, the coil diameter of the spring portion 5 gradually increases as it goes to the second tissue fixing portion 3 side.

It is preferable that the spring portion 5 be formed so that the number of turns of the metal wire material 1a is an integer number of turns that is equal to or greater than a single turn. "Integer number of turns of the single turn" indicates that when the tissue fastener 1 is viewed from the first tissue fixing portion 2 toward the second tissue fixing portion 3, the end portion of the spring portion 5 on the first tissue fixing portion 2 side and the end portion thereof on the tissue pressing portion 6 side are positioned on a straight line that is parallel to the center axis line of the first tissue fixing portion 2 and the second tissue fixing portion 3.

If the spring portion 5 has an integer number of turns equal to or greater than the single turn, when the tissue fastener 1 is viewed in the cross-section parallel to the direction of an axial line passing through the center of the first tissue fixing portion 2 and the second tissue fixing portion 3, the spring portion 5 is in a state of being evenly distributed to the outside in the diameter direction of the first tissue fixing portion 2 and the second tissue fixing portion 3.

Therefore, in a case where the tissue fastener 1 is held in a tissue, the axis of the tissue pressing portion 6 is not deviated from the first tissue fixing portion 2 and the second tissue fixing portion 3, and the shape of the tissue fastener 1 may be stabilized. In this embodiment, as an example, a state where the spring portion 5 is set to a single turn is described. However, the spring portion 5 may be set to two or more turns as long as the turns are an integer number of turns.

As illustrated in FIG. 3, in the tissue pressing portion 6, the metal wire material 1a is loosely wound from the connection portion between the spring portion 5 and the tissue pressing portion 6 and is formed to extend in a cylindrical coil shape having two turns with a coil diameter greater than that of the spring portion 5. In the tissue pressing portion 6, the coil diameters of the two turns of the metal wire material 1a are the same.

In addition, the coil diameter of the second turn of the tissue pressing portion 6 may be smaller than that of the first turn of the tissue pressing portion 6. That is, when viewed in the direction of the center axis line, the maximum outside diameter of a part of the tissue pressing portion 6 in which the number of turns of the metal wire material 1a exceeds the single turn as being measured from the end portion of the spring portion 5 may be equal to or less than the maximum outside diameter of a part of the tissue pressing portion 6 in which the number of turns of the metal wire material 1a is equal to or smaller than the single turn as being measured from the end portion of the spring portion 5.

In this case, in the tissue pressing portion 6, the end portion of the metal wire material 1a is positioned inside the first turn of the metal wire material 1a. Therefore, when the tissue fastener 1 is held in the living tissue, an end portion 6a of the metal wire material 1a is not exposed to the outside and the end portion 6a may be prevented from catching a body wall.

As illustrated in FIGS. 4A and 4B, in an unloaded state in which an external force is not exerted on the tissue pressing portion 6, the metal wire material 1a of the tissue pressing portion 6 is not on a single plane at any position. That is, in the tissue pressing portion 6, the metal wire material 1a is wound in a helical shape. In other words, in the tissue pressing portion 6, the metal wire material 1a is wound not in a spiral shape which is two-dimensional but in a helical shape which is three-dimensional. In use of the tissue fastener 1, as illustrated in FIG. 4B, the metal wire material of the tissue pressing portion 6 is brought into close contact. This differs from, for example, a case where a metal wire material (hereinafter, referred to as "end turn portions 6A and 6B") in a tissue fastener according to the related art illustrated in FIG. 5 is formed along a single plane in an unloaded state.

As illustrated in FIGS. 1 and 3, the terminal of the end portion 6a of the metal wire material 1a in the tissue pressing portion 6 is formed in a hemispheric shape and is bent toward the first tissue fixing portion 2 and the second tissue fixing portion 3 so as to deviate from the loop of the tissue pressing portion 6.

In addition, as illustrated in FIG. 6, when the tissue pressing portion 6 is compressed and deformed in the direction of the center axis line of the coil, at the boundary part between the first and second turns of the tissue pressing portion 6, a bending portion 7 is provided which is formed by bending the metal wire material 1a in a crank shape by a length equal to the outside diameter of the metal wire material 1a. Although details are described later, in use of the tissue fastener 1, the first and second turns of the tissue pressing portion 6 are configured to be capable of intersecting each other at the bending portion 7.

Accordingly, in the state where the metal wire material 1a in the tissue pressing portion 6 comes in contact with the bending portion 7, the end portion 6a of the metal wire material 1a may sit on the first turn of the tissue pressing portion 6 so as to be positioned further towards the spring portion 5 side than the first turn of the tissue pressing portion 6. Accordingly, the possibility of a living tissue being caught on the terminal of the metal wire material 1a in the tissue pressing portion 6 can be reduced.

As illustrated in FIG. 6, the metal wire material 1a of the tissue pressing portion 6 intersects at the bending portion 7. Then, as illustrated in FIG. 7A, the metal wire material 1a of the first turn of the tissue pressing portion 6 becomes the lowest layer coming in contact with the living tissue. In addition, the second turn of the metal wire material 1a sits on the first turn of the metal wire material 1a of the tissue pressing portion 6.

Moreover, in the state where the metal wire material 1a in the tissue pressing portion 6 intersects at the bending portion 7, as illustrated in FIG. 7B, the intersecting metal wire material 1a is maintained in the intersecting state even in the state where an external force is not exerted on the tissue fastener 1. The end portion 6a of the metal wire material 1a is positioned inside the region (regions denoted by reference numeral X1 in FIG. 7A and reference numeral X2 in FIG. 7B) of a truncated cone shape formed by the first tissue fixing portion 2 and the tissue pressing portion 6 of the tissue fastener 1.

Moreover, in the state where the metal wire material 1a in the tissue pressing portion 6 intersects at the bending portion 7, as illustrated in FIG. 7B, in the state where an external force is not exerted on the spring portion 5, both the end portions 3a and 6a of the metal wire material 1a are positioned inside the region (regions denoted by reference numeral X1 in FIG. 7A and reference numeral X2 in FIG. 7B) of a truncated cone shape formed by the first tissue fixing portion 2 and the tissue pressing portion 6 of the tissue fastener 1.

Therefore, by disposing the metal wire material 1a in the tissue pressing portion 6 to intersect at the bending portion 7, the end portions 3a and 6a of the metal wire material 1a may be suppressed from coming in contact with a living tissue.

In addition, as illustrated in FIG. 8, there may be cases where the tissue fastener 1 is held in a living body in the state where the first and second turns of the tissue pressing portion 6 do not intersect each other. In this case, in the tissue pressing portion 6, the end portion 6a of the metal wire material 1a is directed further towards the spring portion 5 side than the second turn of the metal wire material 1a coming in contact with the living tissue. Therefore, when the tissue fastener 1 is held in the living tissue, the end portion 6a of the metal wire material 1a may be prevented from coming in contact with the living tissue.

Next, a production method of the tissue fastener 1 of this embodiment will be described.

Figure 9:
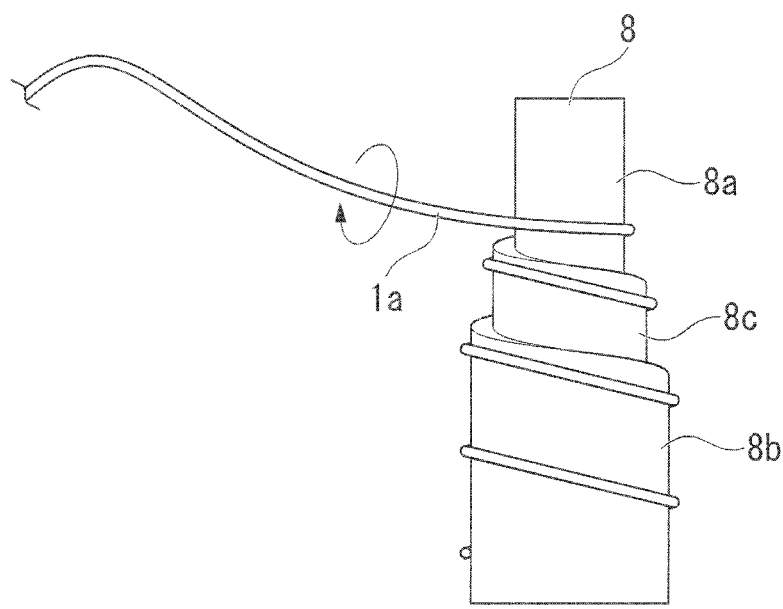
FIG. 9 is a process explanatory view illustrating a tissue fastener production method of this embodiment.

In order to produce the tissue fastener 1, as illustrated in FIG. 9, a production tool 8 is used. The production tool 8 includes two columnar surfaces 8a and 8b having different outside diameters from each other, and a helical surface 8c in a helical shape for connection between the columnar surfaces. The production tool 8 is formed by combining the columnar surfaces 8a and 8b and the helical surface 8c so that the center axis lines thereof are positioned on the coaxial line.

The columnar surface 8a which is relatively thin in the production tool 8 defines the coil diameters of the first tissue fixing portion 2 and the second tissue fixing portion 3. The columnar surface 8a is the outer peripheral surface of a shaft body in a columnar shape having an outside diameter that is substantially the same as the inside diameters of the first tissue fixing portion 2 and the second tissue fixing portion 3.

The helical surface 8c of the production tool 8 defines the coil diameter of the spring portion 5. The helical surface 8c is formed in a helical shape of which the outside diameter is gradually increased from the columnar surface 8a to the columnar surface 8b.

The columnar surface 8b which is relatively thick in the production tool 8 defines the coil diameter of the tissue pressing portion 6. The columnar surface 8b is the outer peripheral surface of a shaft body in a columnar shape having an outside diameter that is substantially the same as the inside diameters of the tissue pressing portion 6.

In addition, the outside diameters of the two shaft bodies in the production tool 8 are appropriately adjusted in consideration of a heat treatment performed on the metal wire material 1a wound around each of the outer peripheral surfaces 8a and 8b of the shaft bodies. Specifically, the coil diameters are changed depending on the type of the material or the temperature of the heat treatment when the heat treatment is performed. In consideration of this, the outside diameters of the two shaft bodies in the production tool 8 are appropriately adjusted so that the metal wire material 1a after the heat treatment has the coil diameters of the first tissue fixing portion 2, the second tissue fixing portion 3, and the tissue pressing portion 6.

A method of producing the tissue fastener 1 using the production tool 8 described above will be described.

First, in a step (forming step) S1 of forming a coil, as illustrated in FIG. 9, the metal wire material 1a is wound around the outer surface of the production tool 8.

In the step S1, initially, one end of the metal wire material 1a is fixed to the outer surface of the columnar surface 8b. Even though the one end of the metal wire material 1a is fixed to any of the two columnar surfaces 8a and 8b in the production tool 8, the tissue fastener 1 may be produced. In this embodiment, an example in which the one end of the metal wire material 1a is fixed to the columnar surface 8b which is relatively thick will be described.

Next, the metal wire material 1a is sinistrally wound around the columnar surface 8b in the periphery of the center axis line of the production tool 8, thereby forming a sinistrally, loosely wound coil directed toward the helical surface 8c side. Specifically, the metal wire material 1a is wound in a winding direction in which the metal wire material 1a is directed counterclockwise from the columnar surface 8b to the columnar surface 8a when viewed from the columnar surface 8b toward the columnar surface 8a. That is, when the center axis of the shaft body is in the vertical direction, the metal wire material 1a is wound around the outer periphery of the shaft body so that the metal wire material 1 viewed on the near side is directed to the upper left from the lower right.

Here, the metal wire material 1a is wound around the columnar surface 8b so as not to cause the metal wire material 1a to have a twisting force round the center axis line of the metal wire material. In this embodiment, the metal wire material 1a is wound around the columnar surface 8b by adjusting the pitch of the metal wire material 1a so that the metal wire material 1a reaches the helical surface 8c when two turns of the metal wire material 1a are wound.

Next, the metal wire material 1a is wound around the helical surface 8c. In this embodiment, as the metal wire material 1a is wound around the helical surface 8c, the coil diameter thereof gradually reduces from the outside diameter of the relatively thick columnar surface 8b to the outside diameter of the relatively thin columnar surface 8a. In this embodiment, the metal wire material 1a is wound around the helical surface 8c by adjusting the pitch of the metal wire material 1a so that the metal wire material 1a reaches the columnar surface 8a when a single turn of the metal wire material 1a is wound around the helical surface 8c.

Next, the metal wire material 1a is sinistrally wound around the columnar surface 8a in the periphery of the center axis line of the production tool 8, thereby forming a sinistrally, closely wound coil directed in a direction further away from the helical surface 8c. Here, the metal wire material 1a is wound around the outer surface of the columnar surface 8a while twisting the metal wire material 1a round the center axis line of the metal wire material 1a.

In this embodiment, the metal wire material 1a is twisted clockwise when viewed from the free end side of the metal wire material 1a, which is the terminal on the opposite side to the one end of the metal wire material 1a fixed to the production tool 8 toward the coil side wound around the columnar surface 8a along the center axis of the metal wire material 1a. That is, the metal wire material 1a is twisted clockwise when viewed from the free end side of the metal wire material 1a toward the shaft body before being wound around the shaft body.

As such, by twisting the metal wire material 1a, initial tension is imparted to the closely wound coil. In this embodiment, while the metal wire material 1a is twisted as described above, six turns thereof are wound around the columnar surface 8a of the production tool 8.

Figure 10:
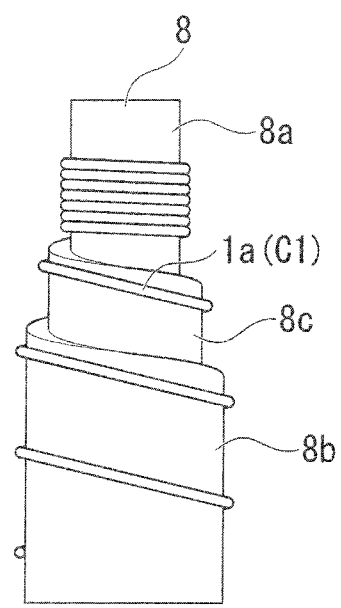
FIG. 10 is a process explanatory view illustrating the tissue fastener production method of this embodiment.

In the state where the metal wire material 1a is wound around the production tool 8, as illustrated in FIG. 10, a sinistrally wound coil C1 is formed of the metal wire material 1a.

Figure 11:
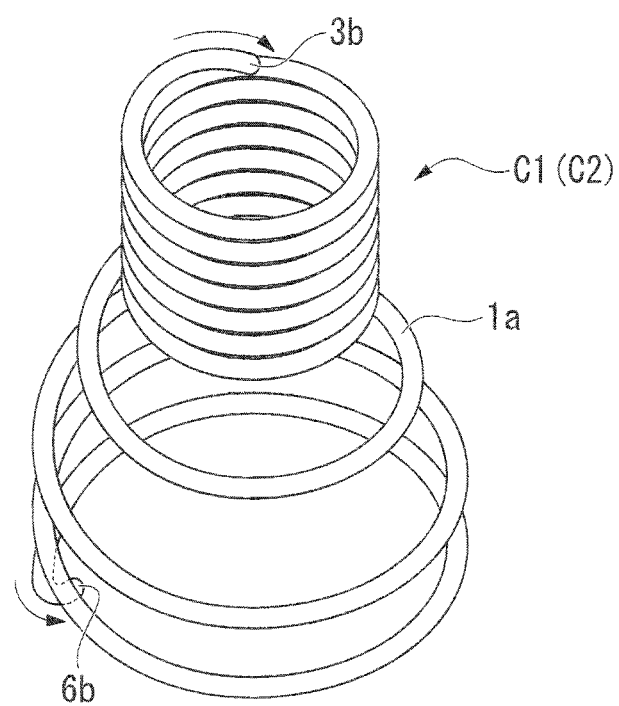
FIG. 11 is a process explanatory view illustrating the tissue fastener production method of this embodiment.

When winding of the metal wire material 1a is completed, the metal wire material 1a is detached from the production tool 8 in the state where the metal wire material 1a maintains the coil shape. Subsequently, as illustrated in FIG. 11, the end portion 3b (a part that is to be the end portion 3a of the second tissue fixing portion 3 later) of the metal wire material 1a on the side wound around the columnar surface 8a is bent toward the inside of the coil. Here, the terminal of the metal wire material 1a is disposed at a position displaced to the inside of the coil by a distance equal to or greater than the diameter of the metal wire material 1a.

Moreover, the end portion 6b (the part that is to be the end portion 6a of the tissue pressing portion 6 later) of the part of the metal wire material 1a wound around the columnar surface 8b is bent so that the terminal of the metal wire material 1a is directed to the region inside the spring portion 5. In addition, bending of the end portions 3b and 6b of the metal wire material 1a may be performed after a step S2 of performing a heat treatment described later.

The step S1 ends here and the step (heat treatment step) S2 of performing a heat treatment is advanced to.

In the step S2, a heat treatment is performed on the coil made of the metal wire material 1a in the state where the metal wire material 1a maintains the coil shape. In this embodiment, after the coil is heated at a predetermined temperature that imparts superelasticity to a metal wire material 1 so as to cause the metal wire material 1a to have superelasticity at room temperature, the coil is rapidly cooled. Accordingly, the coil formed in the step S1 of forming the coil becomes a superelastic coil C2 to which the superelasticity is imparted.

The step S2 ends here and a step (rewinding step) S3 of winding the coil in the reverse direction is advanced to.

Figure 12A:
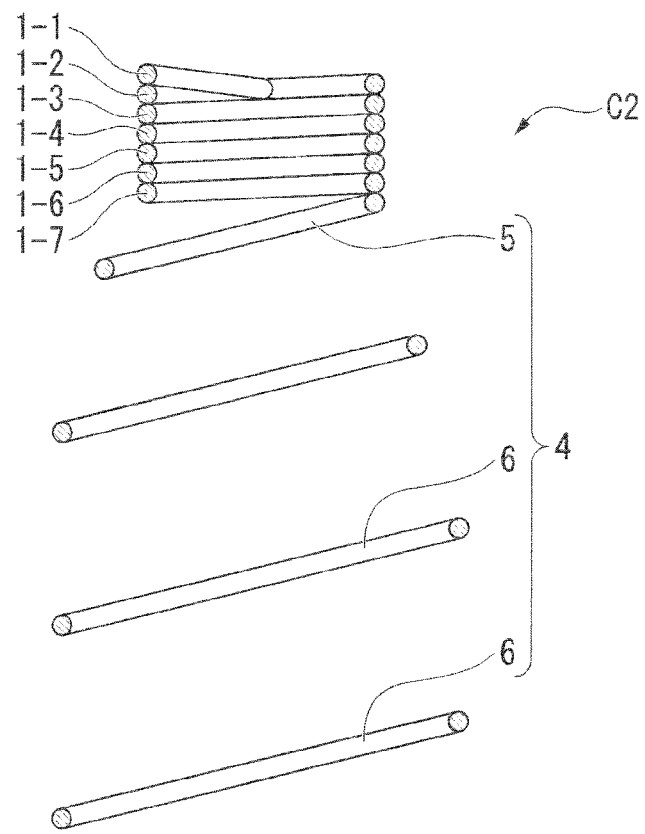
FIG. 12A is a process explanatory view illustrating the tissue fastener production method of this embodiment.
Figure 12B:
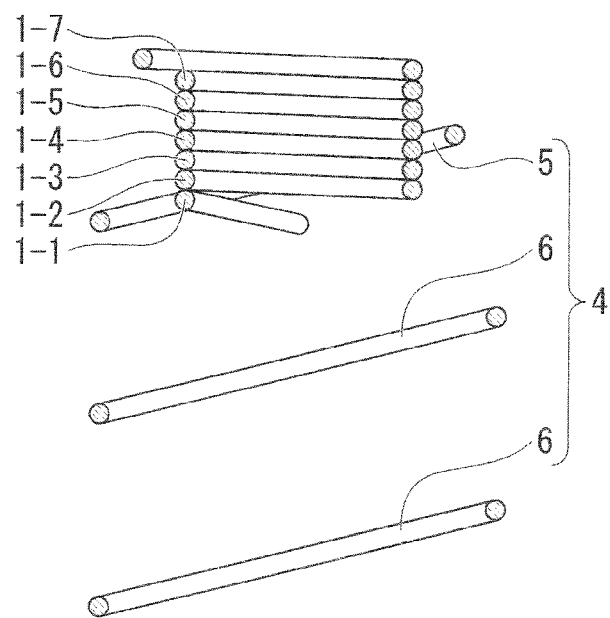
FIG. 12B is a process explanatory view illustrating the tissue fastener production method of this embodiment.

In the step S3, as illustrated in FIGS. 12A and 12B, in the superelastic coil C2 to which the superelasticity is imparted, the winding direction of the metal wire material 1a (denoted by reference numerals 1-1 to 1-7 in FIG. 12A) which is to be the first tissue fixing portion 2 and the second tissue fixing portion 3 is reversed to the outer circumference spring portion 4. That is, the metal wire material 1a is deformed in an elastically deformable range, and the metal wire material 1a is changed from a state arranged in order from 1-1, 1-2, . . . , to 1-7 from the upper side to the lower side to a state arranged in order from 1-7, 1-6, . . . , to 1-1 from the upper side to the lower side. Accordingly, the winding direction of the coil of the part that is to be the first tissue fixing portion 2 and the second tissue fixing portion 3 is reversed to the winding direction of the coil wound in the step S1 of forming the coil.

Here, the metal wire material 1a is not uncoiled to a linear state, and the metal wire material 1a is drawn in the coil in order of turn from the first tissue fixing portion 2 side or the second tissue fixing portion 3 side so as to be displaced, such that the arrangement of the metal wire material 1a is changed. Accordingly, without the superelastic coil C2 being subjected to plastic deformation, the arrangement thereof may be changed. As a result, the superelastic coil C2 becomes a double coil in which the first tissue fixing portion 2 and the second tissue fixing portion 3 are the dextrally wound coil and the outer circumference spring portion 4 is the sinistrally wound coil.

In the step S3 of reversing the winding direction of the metal wire material 1a, the arrangement of the metal wire material 1a is changed, and initial tension is imparted to the first tissue fixing portion 2 and the second tissue fixing portion 3. However, before the step S3, initial tension is imparted to the first tissue fixing portion 2 and the second tissue fixing portion 3. Since the winding direction is reversed in the step S3, after the step S3, the initial tension of the first tissue fixing portion 2 and the second tissue fixing portion 3 is weakened compared to a case where the metal wire material 1a is wound around the production tool 8 while the metal wire material 1a is not twisted in the step S1 of forming the coil and the winding direction of the metal wire material 1a is reversed.

In this embodiment, the winding direction of the superelastic coil C2 to which the initial tension is imparted by twisting the metal wire material 1a is reversed. In this manner, an initial tension having a different magnitude from that of a case where the metal wire material 1a is not twisted and the winding direction is reversed after the superelastic coil C2 is formed may be imparted to the superelastic coil C2.

It is known that in the case where a coil is formed by winding a metal wire material 1a, initial tension is imparted to the coil by twisting the metal wire material 1a. However, in the case where initial tension is imparted to the coil by twisting the metal wire material 1a, the coil may not be formed when the metal wire material 1a is twisted until the metal wire material 1a is twisted off. Therefore, the amount of the metal wire material 1a twisted has an upper limit. Accordingly, the initial tension that may be imparted to the coil only by twisting the metal wire material 1a has an upper limit.

In addition, it is also known that in a coil on which initial tension is not exerted, when the winding direction of a metal wire material is reversed after forming the coil, the coil has a different initial tension. In addition, in the case where the winding direction of the coil on which initial tension is not applied is reversed, the initial tension of the coil in which the winding direction of the metal wire material is reversed has a magnitude equal to or greater than a certain degree, and thus the initial tension that may be set has a lower limit.

As such, it is difficult to, to a coil, impart an initial tension in a range of greater than the upper limit of the initial tension that may be imparted only by twisting the metal wire material 1a and smaller than the lower limit of the initial tension that may be imparted only by reversely winding the coil. Therefore, in a technique according to related art, there may be cases where, to a coil, an initial tension may not be imparted which is optimal to interpose the coil between living tissues so as to cause the living tissues to be subjected to avascular necrosis by compression for adhesion of both the tissues.

Contrary to this, in this embodiment, the magnitude of the initial tension of the superelastic coil C2 that may be achieved in the step S1 of forming the coil and in the step S2 of performing the heat treatment is determined by the amount of the metal wire material 1a twisted when the metal wire material 1a is initially wound and the winding pitch of the metal wire material 1a. Accordingly, in this embodiment, before the step S3 of reversing the winding direction of the metal wire material 1a, the initial tension is imparted to the superelastic coil C2.

In the production method of the tissue fastener 1 of this embodiment, after increasing the initial tension of the coil by twisting the metal wire material 1a of the coil, the winding direction of the coil is reversed. Accordingly, the initial tension increased by twisting the metal wire material 1a of the coil is exerted to conversely reduce the initial tension by rewinding the coil. In the production method of the tissue fastener 1 of this embodiment, an initial tension that is smaller than the lower limit of the initial tension that may be imparted only by rewinding the coil may be imparted to the coil.

As a result, according to the production method of the tissue fastener 1 of this embodiment, there is an advantage that, to the coil, an initial tension may be imparted which is in a range of greater than the upper limit of the initial tension obtained only by twisting the coil and smaller than the lower limit of the initial tension obtained only by reversely winding the coil. In addition, according to the tissue fastener 1 produced by the production method of the tissue fastener of this embodiment, to the coil, an initial tension may be imparted which is optimal to interpose the coil between living tissues so as to cause the living tissues to be subjected to avascular necrosis by compression for adhesion of both the tissues.

Next, a configuration example of an applicator 10 for placing the tissue fastener 1 of this embodiment in a living tissue will be described.

Figure 13A:
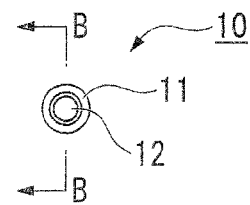
FIG. 13A is a front view illustrating a configuration example of an applicator used in a procedure in which the tissue fastener of this embodiment is used.
Figure 13B:
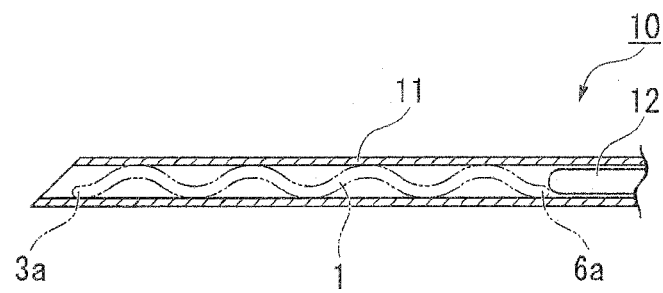
FIG. 13B is a cross-sectional view taken along the line B-B of FIG. 13A.
Figure 13C:
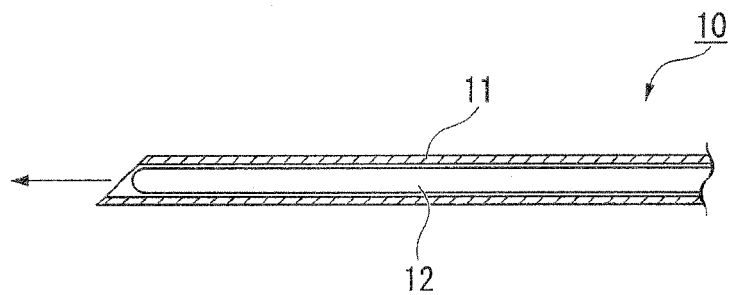
FIG. 13C is an operation explanatory view for explaining the operation of the applicator in use.

FIG. 13A is a front view of the applicator 10. FIG. 13B is a cross-sectional view taken along the line B-B of FIG. 13A. FIG. 13C is an explanatory view for explaining operations of the applicator 10.

As illustrated in FIGS. 13A to 13C, the applicator 10 includes a needle tube 11 which has a cylindrical shape and is sharply formed in a shape in which the distal end is obliquely cut, and a pushrod 12 inserted into the needle tube 11 so as to advance or retreat. Although not shown in the figure, the pushrod 12 protrudes from the proximal end of the needle tube 11 and is configured so that an operation of causing the pushrod 12 at the proximal end of the needle tube 11 to advance or retreat with respect to the needle tube 11 is allowed.

Inside the needle tube 11, the tissue fastener 1 may be inserted and held in a state of being uncoiled. The outside diameter of the needle tube 11 has a size so as to be inserted into, for example, an instrument channel 22 (see FIG. 14) of an ultrasonic endoscope 20 described later. In addition, in order to protect the inner wall of the instrument channel 22 of the ultrasonic endoscope 20 from the distal end of the needle tube 11 sharply formed, the applicator 10 may include a sheath tube 13 (see FIG. 14) through which the needle tube 11 is inserted.

Next, a procedure of providing a fistula between a duodenum Dd and a common bile duct Cb using the tissue fastener 1 of this embodiment and the applicator 10 of the configuration example will be described. The procedure of providing the fistula in this embodiment is to adhere the duodenum Dd and the common bile duct Cb to each other and form a through-hole at the adhered part.

Figure 18:
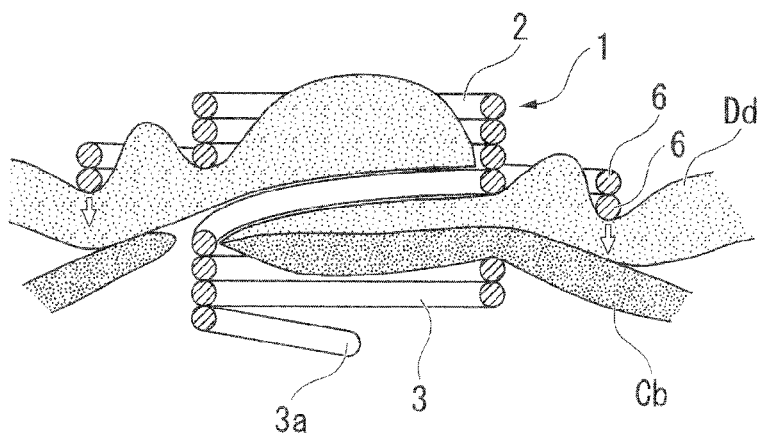
FIG. 18 is a cross-sectional view illustrating the tissue fastener of this embodiment, which fixes a duodenum and a common bile duct to each other and is held in a living body.
Figure 19:
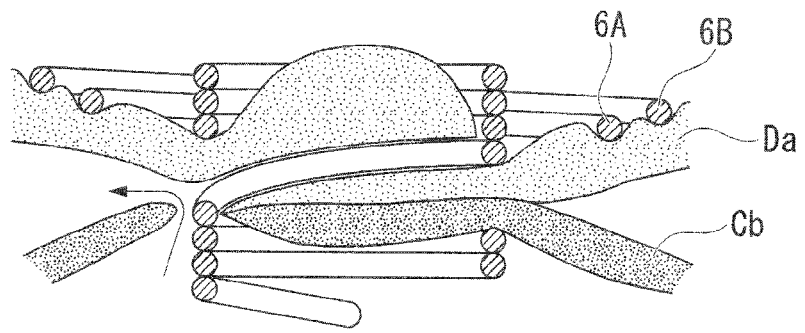
FIG. 19 is a cross-sectional view illustrating a tissue fastener according to related art in a case where the tissue fastener according to the related art is held in a living body as illustrated in FIG. 18.

FIGS. 14 to 17 are explanatory views showing stages of the procedure in this embodiment. FIG. 18 is a cross-sectional view illustrating the tissue fastener of this embodiment, which fixes the duodenum Dd and the common bile duct Cb to each other and is held in a living body. FIG. 19 is a cross-sectional view illustrating a tissue fastener according to related art in a case where the tissue fastener according to the related art is held in a living body as illustrated in FIG. 18.

Figure 14:
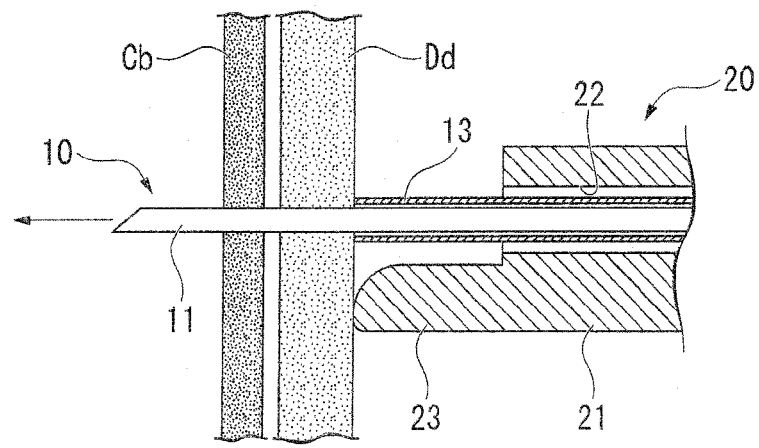
FIG. 14 is an explanatory view illustrating a stage of the procedure using the applicator.

In this embodiment, the tissue fastener 1 and the applicator 10 are used together with the linear scanning type ultrasonic endoscope 20 having, for example, a forceps channel. As illustrated in FIG. 14, the ultrasonic endoscope 20 includes a flexible insertion portion 21 inserted into a body, the instrument channel 22 provided inside the insertion portion 21, an ultrasonic observation unit 23 provided to the distal end of the insertion portion 21, and an operation unit (not shown) provided to the proximal end of the insertion portion 21. The instrument channel 22 is configured to insert the needle tube 11 so as to advance and retreat and to expose the needle tube 11 from the distal end of the insertion portion 21.

In addition, the ultrasonic observation unit 23 is configured to emit ultrasonic waves from the distal end of the insertion portion 21 using an ultrasonic vibrator (not shown), receive reflection waves reflected from, for example, a living tissue, transmit a signal to a monitor (not shown) or the like, and form an image on the monitor.

In addition, at the distal end of the insertion portion 21 in the ultrasonic endoscope 20, optical observation device (not shown) having a field of view toward the front from the distal end of the insertion portion 21 is provided. In this embodiment, the observation device includes an imaging lens group and a solid-state imaging element inside the distal end of the insertion portion 21. The solid-state imaging element of the observation device is configured to transmit an image signal to the monitor described above or a monitor additionally installed outside the body.

In addition, the configuration of the ultrasonic endoscope 20 is not limited to a configuration including the ultrasonic observation unit 23 and may be a configuration including other probe type ultrasonic devices. In addition, instead of the ultrasonic endoscope 20, an endoscope that performs observation using means other than ultrasonic waves may also be used. In this case, it is preferable that the inside of a body cavity be observed also using a device, such as an ultrasonic device, used outside the body, an X-ray apparatus, a magnetic resonance imaging apparatus (MRI) apparatus, or a computed tomography apparatus (CT apparatus).

Hereinafter, a procedure of performing a treatment by combining the applicator 10 and the tissue fastener 1 of this embodiment with the ultrasonic endoscope 20 described above will be described by exemplifying a procedure of fixing the duodenum Dd to the common bile duct Cb in one body and providing a through-hole to cause the two to communicate with each other as an example of a transduodenal jaundice treatment.

This procedure is a jaundice treatment performed in a case where bile cannot be discharged from a duodenal papilla due to biliary obstruction or the like caused by a tumor and the bile is dissolved in blood and causes jaundice. An object of the procedure is to discharge the bile directly to the duodenum Dd from the common bile duct Cb.

Before starting the procedure, the tissue fastener 1 in a semi-finished product state achieved at the time point when the step S2 of performing the above-described heat treatment ends, or the tissue fastener 1 for which the step S3 of reversing the winding direction of the metal wire material 1a ends is loaded in the needle tube 11 of the applicator 10. Here, as illustrated in FIG. 13B, the tissue fastener 1 is uncoiled and is loaded in the needle tube 11 so that, regarding the end portions of the metal wire material 1a constituting the tissue fastener 1, the end portion 6a on the tissue pressing portion 6 side is positioned on the proximal end side of the needle tube 11, and the end portion 3a on the second tissue fixing portion 3 side is positioned on the distal end side of the needle tube 11. In this state, the applicator 10 is provided to the procedure.

When the procedure is started, first, the insertion portion 21 of the ultrasonic endoscope 20 is manually inserted into the body of a patient from the distal end by an operator. In this embodiment, the insertion portion 21 of the ultrasonic endoscope 20 is inserted into the duodenum Dd which is an upper gastrointestinal tract from the mouth which is a natural opening of the patient. When the insertion portion 21 of the ultrasonic endoscope 20 reaches the duodenum Dd, the state of the outside of the lumen of the duodenum Dd is observed using the ultrasonic observation unit 23, and the operator determines an appropriate position to provide a fistula as a position close to the common bile duct Cb in a region further towards the stomach side than the duodenal papilla.

After the appropriate position to provide the fistula is determined, the operator inserts the needle tube 11 of the applicator 10 into the instrument channel 22 of the ultrasonic endoscope 20 from the distal end, and exposes the distal end of the needle tube 11 from the distal end of the insertion portion 21 of the ultrasonic endoscope 20. The needle tube 11 exposed from the distal end of the insertion portion 21 of the ultrasonic endoscope 20 may be observed using the optical observation device.

Subsequently, the operator scans the common bile duct Cb over the duodenum Dd using the ultrasonic observation unit 23 provided in the ultrasonic endoscope 20 and determines a position to cause the needle tube 11 to pierce through and be inserted into the duodenum Dd and the common bile duct Cb.

When the position where the needle tube 11 is pierced and inserted is determined, as illustrated in FIG. 14, the needle tube 11 is pushed forward from the ultrasonic endoscope 20. In addition, the tubular walls of the duodenum Dd and the common bile duct Cb are penetrated by the needle tube 11 so that the distal end of the needle tube 11 is positioned inside the lumen of the common bile duct Cb. Here, a stopper or the like that appropriately adjusts the length of the needle tube 11 pierced may be mounted in the applicator 10 in advance. When the stopper is provided in the applicator 10, the piercing amount of the needle tube 11 may be prevented from being excessive or insufficient.

Figure 15:
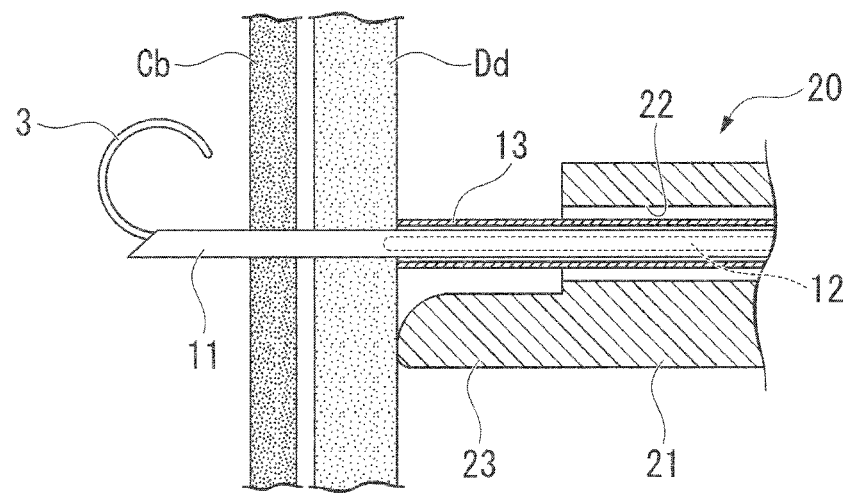
FIG. 15 is an explanatory view illustrating a stage of the procedure using the applicator.
Figure 16:
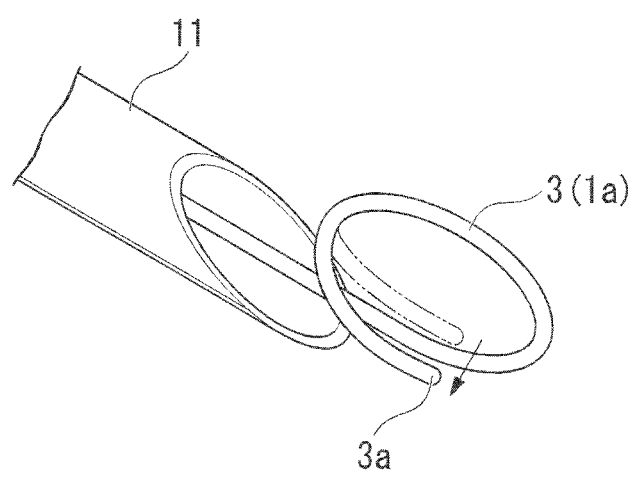
FIG. 16 is an operation explanatory view for explaining the operation of the tissue fastener pushed out from a needle tube in the procedure using the applicator.

As illustrated in FIG. 15, when the distal end of the needle tube 11 is disposed in the inner cavity of the common bile duct Cb, the operator moves the pushrod 12 forward with respect to the needle tube 11 and pushes out the second tissue fixing portion 3 in the tissue fastener 1 from the distal end of the needle tube 11. The second tissue fixing portion 3 pushed out from the distal end of the needle tube 11 is returned to the coil shape by its superelasticity. Here, as illustrated in FIG. 16, the metal wire material 1a bent at the end portion 3a of the wire material in the second tissue fixing portion 3 comes in contact with the outer surface of the metal wire material 1a at a position of the first turn measured toward the first tissue fixing portion 2, and the end portion 3a of the metal wire material 1a is pressed against the outer surface of the metal wire material 1a.

Then, the end portion 3a of the metal wire material 1a slides along the outer surface of the metal wire material 1a, and the winding direction of the metal wire material 1a at the second tissue fixing portion 3 restored to the coil shape is uniquely determined. In this embodiment, the winding direction of the metal wire material 1a when the second tissue fixing portion 3 returned to the coil shape is reversed to the winding direction of the metal wire material 1a wound around the production tool 8 in the forming step S1 in the production method of the tissue fastener 1.

That is, the second tissue fixing portion 3 sinistrally wound in the forming step S1 in the production method described above becomes a dextrally wound coil when being pushed out from the distal end of the needle tube 11 and returned to the coil shape. Therefore, even though the tissue fastener 1 loaded in the needle tube 11 is a semi-finished product that is not subjected to the step S3 of reversing the winding direction of the metal wire material 1a, the step S3 is performed on the second tissue fixing portion 3 as the first tissue fixing portion 2 is pushed out from the needle tube 11.

Even in the tissue fastener 1 subjected to the step S3 before being loaded in the needle tube 11, the tissue fastener 1 is returned to a right shape after the step S3 ends.

When the second tissue fixing portion 3 is returned to the coil shape in the inner cavity of the common bile duct Cb, the operator draws the needle tube 11 back with respect to the ultrasonic endoscope 20. Then, the needle tube 11 is drawn out of the tubular wall of the duodenum Dd and the tubular wall of the common bile duct Cb, and only the second tissue fixing portion 3 is disposed in the lumen of the common bile duct Cb.

Figure 17:
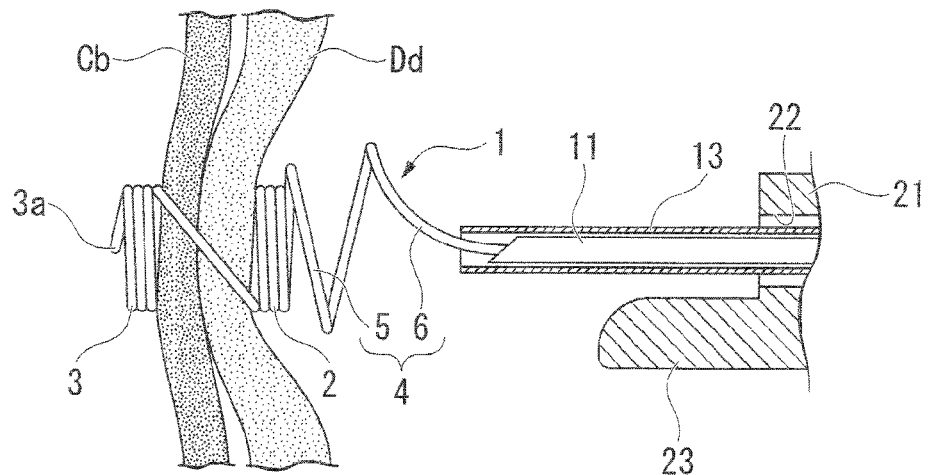
FIG. 17 is an explanatory view illustrating a stage of the procedure using the applicator.

Moreover, as illustrated in FIG. 17, in the state where the distal end of the needle tube 11 is positioned inside the lumen of the duodenum Dd, the operator pushes the pushrod 12 forward with respect to the needle tube 11 and pushes out the first tissue fixing portion 2 and the outer circumference spring portion 4 from the distal end of the needle tube 11. Then, the first tissue fixing portion 2 is returned to a coil in the same winding direction as the winding direction of the coil to which the second tissue fixing portion 3 is returned.

That is, the first tissue fixing portion 2 pushed out from the distal end of the needle tube 11 is a dextrally wound coil. Accordingly, the winding direction of the metal wire material 1a in the first tissue fixing portion 2 and the second tissue fixing portion 3 is a dextral direction which is reverse to the sinistral direction that is the winding direction in the step S1 of forming the coil described above, so that the step S3 for the first tissue fixing portion 2 and the second tissue fixing portion 3 ends.

In addition, since the metal wire material 1a of the tissue fastener 1 is returned to the coil shape, when the first tissue fixing portion 2 is pushed out from the needle tube 11, the shape of the metal wire material 1a is gradually returned from a part thereof close to the duodenum Dd. Accordingly, without the metal wire material 1a of the tissue fastener 1 being entangled, the second tissue fixing portion 3, the spring portion 5, and the tissue pressing portion 6 are formed on the duodenum Dd side.

As illustrated in FIG. 18, after all the metal wire material of the tissue fastener 1 is pushed out from the distal end of the needle tube 11, the tissue pressing portion 6 of the outer peripheral portion 4 in the tissue fastener 1 presses the tubular wall of the duodenum Dd against the common bile duct Cb side from the duodenum Dd side by its own elasticity and the elasticity of the spring portion 5. Here, two turns of the metal wire material 1a in the tissue fixing portion 6 come in close contact with each other, and each part of the metal wire material 1a presses the tubular wall of the duodenum Dd against the common bile duct Cb side from the duodenum Dd side.

FIG. 19 illustrates a case where a duodenum Dd and a common bile duct Cb are fixed by a tissue fastener according to the related art in which an end turn portion is formed as described above. In the tissue fastener according to the related art where the end turn portion is formed in an outer circumference spring portion, an end turn portion 6B of a second turn when viewed from a spring portion is pushed back by the tubular wall of the duodenum Dd and is thus at a position slightly deviated on the inner cavity side of the duodenum Dd with respect to an end turn portion 6A of a first turn. The deviation amount of the end turn portion 6B of the second turn gradually increases toward the outer periphery of the end turn portion 6B.

Therefore, it is thought that in the end turn portion 6B of the second turn in the configuration according to the related art, there is a possibility that a sufficient pressing force to fix the duodenum Dd and the common bile duct Cb may not be applied to the tubular wall of the duodenum Dd. In this case, there is a possibility of a gap being generated between the duodenum Dd and the common bile duct Cb, and there is a concern of bile leaking from the gap to the body cavity.

Contrary to this, in the tissue fastener 1 of this embodiment, since the tissue pressing portion 6 of the outer circumference spring portion 4 is formed in the cylindrical coil shape in which the metal wire material 1a is not on the same plane unlike the end turn, the first and second turns of the metal wire material 1a of the tissue pressing portion 6 are each able to press the tubular wall of the duodenum Dd. Therefore, a possibility of a gap being generated between the duodenum Dd and the common bile duct Cb may further be reduced.

After the tissue fastener 1 is placed, the intestinal wall of the duodenum Dd and the tubular wall of the common bile duct Cb positioned in the first tissue fixing portion 2 and the second tissue fixing portion 3 are tightly fastened by the first tissue fixing portion 2 and the second tissue fixing portion 3. Accordingly, in the duodenum Dd and the common bile duct Cb, the parts inside of the first tissue fixing portion 2 and the second tissue fixing portion 3 impede the bloodstream and cause compression necrosis. Moreover, in the peripheries of the first tissue fixing portion 2 and the second tissue fixing portion 3, the intestinal wall and the tubular wall are adhered and joined to each other.

In addition, the necrosed tissue and the tissue fastener 1 fall off from the holding position where the tissue fastener 1 is placed. Here, the first tissue fixing portion 2 and the second tissue fixing portion 3 are always biased against the inner cavity side of the duodenum Dd by the outer circumference spring portion 4. In addition, since the outer circumference spring portion 4 has an inside diameter greater than the fistula, the outer circumference spring portion 4 is not able to pass through the fistula.

Accordingly, when the tissue fastener 1 falls off from another tissue, the tissue fastener 1 reliably falls off toward the inner cavity side of the duodenum Dd. The tissue fastener 1 that falls off into the inner cavity of the duodenum Dd is excreted from the body through the small and large intestines. Here, since the end portion of the metal wire material 1a in the outer circumference spring portion 4 extends toward the inward direction of the loop of the tissue fastener 1, when the tissue fastener 1 moves through the gastrointestinal tract, the end portion of the metal wire material 1a does not come in contact with the tissues and damage the tissues.

While the exemplary embodiments of the invention have been described, the invention is not limited to these embodiments. Additions, omissions, substitutions, and modifications of the configuration can be made in a range without departing from the gist of the invention.

For example, in the production method of the tissue fastener 1 described above, an example in which, in the state where the step S3 of reversing the winding direction of the metal wire material 1a ends, the first tissue fixing portion 2 and the second tissue fixing portion 3 are dextrally wound coils and the outer circumference spring portion 4 is a sinistrally wound coil is illustrated. However, there may be cases where the tissue fastener 1 in which the first tissue fixing portion 2 and the second tissue fixing portion 3 are sinistrally wound coils and the outer circumference spring portion 4 is a dextrally wound coil is produced. That is, when a helical surface 8c rewound from the production tool 8 described above is provided by changing the shape of the production tool 8, the tissue fastener 1 may be easily produced, and the same effects as those of the above-described embodiments are present.

In addition, in the production method of the tissue fastener 1 in the embodiment described above, in the step S1 of forming the coil, the metal wire material 1a that is to be the first tissue fixing portion 2 and the second tissue fixing portion 3 later is closely wound. However, the invention is not limited to this, and the metal wire material 1a in the step S1 may be loosely wound. Moreover, even when a loosely wound coil is made in the Step S1, the metal wire material 1a may be wound around the production tool 8 while being twisted round the center axis line of the metal wire material.

Specifically, in the step S1 of forming the coil, the one end of the metal wire material 1a is fixed to the shaft body, and the metal wire material 1a may be wound around the outer periphery of the shaft body while opening a gap from the adjacent metal wire material 1a.

By performing the forming step S1 by appropriately changing the winding pitch, twisting direction, and twisting amount of the metal wire material 1a, a tissue fastener in which a different initial tension is set for the first tissue fixing portion 2 and the second tissue fixing portion 3 after the step S3 of reversing the winding direction of the metal wire material 1a ends may be appropriately produced.

Specifically, in the step S1 of forming the coil, the twisting direction of the metal wire material 1a round the axis of the metal wire material 1a may be determined depending on a direction in which the metal wire material is wound around the shaft body in the step S1.

That is, in the step S1 of forming the coil, in the case where the metal wire material 1a is dextrally wound, the metal wire material 1a is twisted counterclockwise when viewed from the free end side of the metal wire material 1a toward the shaft body before being wound around the shaft body.

Contrary to this, in the step S1 of forming the coil, in the case where the metal wire material 1a is sinistrally wound, the metal wire material 1a is twisted clockwise when viewed from the free end side of the metal wire material 1a toward the shaft body before being wound around the shaft body.

In addition, in the case where the metal wire material 1a is dextrally wound, the metal wire material 1a may be twisted clockwise when viewed from the free end side of the metal wire material 1a toward the shaft body before being wound around the shaft body.

In addition, the outer circumference spring portion may not be necessary in order to obtain an initial tension between the upper limit and the lower limit described above for each of the first tissue fixing portion 2 and the second tissue fixing portion 3. Even in the tissue fastener 1 without the outer circumference spring portion 4, an initial tension may be set in the same manner using the production method described above.

Besides, the invention is not limited to the above description and is limited only by the range of the appended claims.

What is claimed is:

1. A method of producing a tissue fastener which clamps two living tissues into close contact with each other, comprising the steps of:
   a first step of fixing one end portion of a wire made of a metal to a shaft body;
   after the first step, a second step of winding the wire in a predetermined winding direction around an outer periphery surface of the shaft body to form a coil;
   concurrently with the second step, a third step of twisting a portion of the wire forming the coil around an axis of the wire;

after the third step, a fourth step of heat treating the coil to impart superelasticity to the wire forming the coil; and after the fourth step, a fifth step of rewinding at least the portion of the wire that is twisted in a direction reverse to the predetermined winding direction and within an elastically deformable range of the wire to which the superelasticity was imparted in the fourth step.

2. The tissue fastener production method according to claim 1, wherein, in the third step, a twisting direction of the wire around the axis of the wire material is determined depending on the predetermined winding direction of the wire around the shaft body.

3. The tissue fastener production method according to claim 2,
wherein, in the second and third steps, in a case where the wire is dextrally wound, the wire is twisted counterclockwise when viewed from a free end side of the wire toward the shaft body before being wound around the shaft body, and
in a case where the wire is sinistrally wound, the wire is twisted clockwise when viewed from the free end side of the wire toward the shaft body before being wound around the shaft body.

4. The tissue fastener production method according to claim 2,
wherein, in the second and third steps, in a case where the wire is dextrally wound, the wire is twisted clockwise when viewed from a free end side of the wire toward the shaft body before being wound around the outer periphery of the shaft body, and
in a case where the wire is sinistrally wound, the wire is twisted counterclockwise when viewed from the free end side of the wire toward the shaft body before being wound around the shaft body.

5. The tissue fastener production method according to claim 1, wherein, in the second step, the coil is formed which comprises:
a tissue fixing portion having a coil shape;
a spring portion that is connected to the tissue fixing portion, is wound in the same direction as a winding direction of the tissue fixing portion, and is formed in a coil shape with a greater coil diameter than a coil diameter of the tissue fixing portion; and
a tissue pressing portion that is connected to the spring portion, is wound in the same direction as the winding direction of the spring portion, and is formed in a coil shape with a greater coil diameter than the coil diameter of the spring portion.

6. The tissue fastener production method according to claim 5, wherein, in the fifth step, the winding direction of the tissue fixing portion and the winding direction of the spring portion are reversed.

7. The tissue fastener production method according to claim 1, wherein
the shaft body has a columnar surface of which an outside diameter is larger than that of the outer periphery surface,
the second step includes forming a circumference spring portion which is continuously connected to an other end of the coil and which has a larger outside diameter than that of the coil by winding the wire that is continuously connected to the other end of the coil around the columnar surface without twisting, and the fifth step includes rewinding the wire of the coil wound around the outer peripheral surface with respect to the wire of the circumference spring portion in a direction reverse to the winding direction of the coil and such that the winding directions of adjacent wires in the coil are the same in an inner space that is surrounded by the wire forming the circumference spring portion when the circumference spring portion is detached from the columnar surface.

8. The tissue fastener production method according to claim 1, wherein the second step forms the coil on which a predetermined force is exerted in a longitudinal direction of the shaft body and the predetermined force is a force that clamps two living tissues into close contact with each other and causes two living tissues to be subjected to avascular necrosis.

9. A method of producing a tissue fastener which clamps two living tissues into close contact with each other, comprising the steps of:
a first step of fixing one end portion of a wire made of a metal to a shaft body;
after the first step, a second step of winding the wire in a predetermined winding direction around an outer periphery surface of the shaft body to form a coil in which a gap is opened between adjacent loops of the wire;
concurrently with the second step, a third step of twisting a portion of the wire forming the coil around an axis of the wire;
after the third step, a fourth step of heat treating the coil to impart superelasticity to the wire forming the coil;
after the fourth step a fifth step of rewinding at least the portion of the wire that is twisted in a direction reverse to the predetermined winding direction in the first step and in a winding direction and within an elastically deformable range of the wire to which the superelasticity was imparted in the fourth step,
after the fifth step, a sixth step of exerting an initial tension on the wire in a compression direction of the wire.

10. The tissue fastener production method according to claim 9,
wherein, in the second and third steps, in a case where the wire material is dextrally wound, the wire material is twisted counterclockwise when viewed from a free end side of the wire material toward the shaft body before being wound around the shaft body, and
in a case where the wire material is sinistrally wound, the wire material is twisted clockwise when viewed from the free end side of the wire material toward the shaft body before being wound around the shaft body.

11. The tissue fastener production method according to claim 9,
wherein, in the second and third steps, in a case where the wire material is sinistrally wound, the wire material is twisted counterclockwise when viewed from a free end side of the wire material toward the shaft body before being wound around the shaft body, and
in a case where the wire material is dextrally wound, the wire material is twisted clockwise when viewed from the free end side of the wire material toward the shaft body before being wound around the shaft body.

* * * * *